United States Patent [19]

Thomson

[11] Patent Number: 4,592,884

[45] Date of Patent: Jun. 3, 1986

[54] METHOD FOR MAKING SPECIMEN CONTAINERS

[75] Inventor: Loronzo H. Thomson, Warner Robins, Ga.

[73] Assignee: Little Rapids Corp., Green Bay, Wis.

[21] Appl. No.: 588,685

[22] Filed: Mar. 12, 1984

[51] Int. Cl.[4] .............................................. C04B 41/16
[52] U.S. Cl. .................................. 264/132; 264/293; 264/509; 264/537; 428/35; 116/308; 206/459; 206/534; 215/1 R; 215/1 C; 215/230; 215/365; 222/551
[58] Field of Search .......................... 428/35; 116/308; 206/459, 534; 215/1 R, 1 C, 230, 365; 222/551; 264/132, 293, 509, 537

[56] References Cited

U.S. PATENT DOCUMENTS

| | | | |
|---|---|---|---|
| 4,195,059 | 3/1980 | Whitcher et al. | 206/459 |
| 4,301,941 | 11/1981 | Kraft | 206/459 |
| 4,444,329 | 4/1984 | Vollers | 215/230 |

Primary Examiner—Joseph L. Schofer
Assistant Examiner—N. Sarofin
Attorney, Agent, or Firm—Roylance, Abrams, Berdo & Goodman

[57] ABSTRACT

Specimen containers, such as containers for urine specimens, are produced in a manner which assures not only against spillage of the specimen but also against possible confusion as to the source of the specimen.

4 Claims, 7 Drawing Figures

METHOD FOR MAKING SPECIMEN CONTAINERS

This invention relates to methods for making specimen containers, especially containers for urine specimens, in such fashion that the danger of confusion as to the identity of the patient who has given the specimen is reduced.

RELATED APPLICATION

The specimen container disclosed in this application as an example of containers which can be produced according to the invention is also disclosed and claimed in my co-pending application Ser. No. 588,814, filed concurrently herewith.

BACKGROUND OF THE INVENTION

In doctors' offices, analytical laboratories and hospitals it is standard practice to obtain specimens of body fluids, particularly urine, from patients in order to analyze the specimens as an aid to diagnosis. Though the practice of analyzing specimens of urine and other body fluids is very old, handling of the specimens is still done in a crude manner, with the specimens given by the patient into containers of widely varying types, frequently without covers and frequently without any truly dependable means for assuring identification of the specimen as that of a particular patient. Thus, not infrequently, the specimen is collected in a glass bottle, carried about the office open, and simply placed on a piece of paper bearing the patient's name. In some doctors' offices and laboratories, an adhesive label is applied to the side of the bottle and the patient's name written on the label. In other cases, a wide mouth container is used, a cover is provided, and the label is applied to the cover. When open containers are used, the practice is unsanitary, because of spillage of portions of the specimen. When a cover is employed, the danger of spillage is reduced or eliminated, but a danger of confusion of specimens, so that the results of an analysis of one specimen are reported for a patient different from the one who gave that specimen, is generated, since the cover originally applied to one specimen container, and bearing the patient's name, is interchanged inadvertently with the cover from another patient's container. The advent of specimen containers molded from polymeric materials and equipped with removable covers has greatly improved the practice, but no adequate and inexpensive way has yet been provided for minimizing the danger that specimens and patients may be confused because of inadvertent application of the cover from one specimen container to the container of another specimen.

OBJECTS OF THE INVENTION

A general object of the invention is to devise a method for producing specimen containers, of the type comprising a container body and a reclosable cover, in such fashion that the danger of confusing one specimen with another as a result of interchange of two covers is minimized.

Another object is to provide reclosable specimen containers in such fashion that the container bodies and covers are serialized to prevent confusion.

A further object is to devise such a method wherein first indicia applied to the cover and second indicia applied to the container body will always be mutually aligned when, having been removed, the cover is properly replaced.

Yet another object is to devise a container, of the type comprising a container body and a separate cover therefor, in which the container body and cover are marked in a characteristic fashion such that a person handling the container can observe at a glance if the cover on the container body is the correct cover or has been interchanged with the cover for another container body.

SUMMARY OF THE INVENTION

Methods according to the invention are practiced by molding from polymeric material as separate pieces both a hollow container body and a removable cover for closing the top of the container body, the body having a side wall with an outer surface portion constituting a display area, the upper surface of the cover constituting a display area; delivering the body and cover to an assembly station and there applying the cover to the container body while the cover occupies that position relative to the body which is desired for adequate closing of the container body by the cover; applying to the upper surface of the cover first permanent characteristic identifying indicia; applying to the display area of the side wall of the container body second permanent identifying indicia identical to that applied to the cover; and delivering the container body, with the cover still applied thereto, to a packaging station and packaging the container without removal of the cover. Advantageously, the method is practiced in connection with specimen containers having the configuration described and claimed in said copending application Ser. No. 588,814. The method thus provides novel containers comprising a pouring spout and in which serial numbers on the cover and the side wall of the container body below the pouring spout are so located as to assure that both serial numbers can be observed simultaneously when the cover has been applied to the container body.

IDENTIFICATION OF THE DRAWINGS

DETAILED DESCRIPTION OF THE INVENTION

Specimen Container of FIGS. 1–5A

Figure 5:
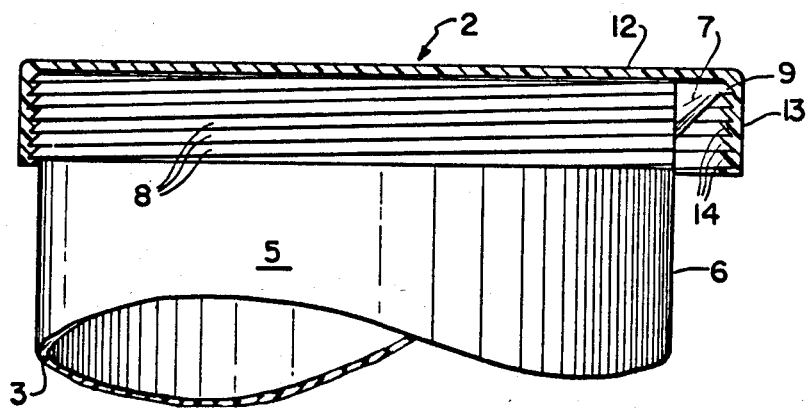
FIG. 5 is a fragmentary view, partly in side elevation and partly in vertical cross section, enlarged with respect to FIGS. 1-4, showing the cover applied to the container body but not fully tightened.
Figure 5A:
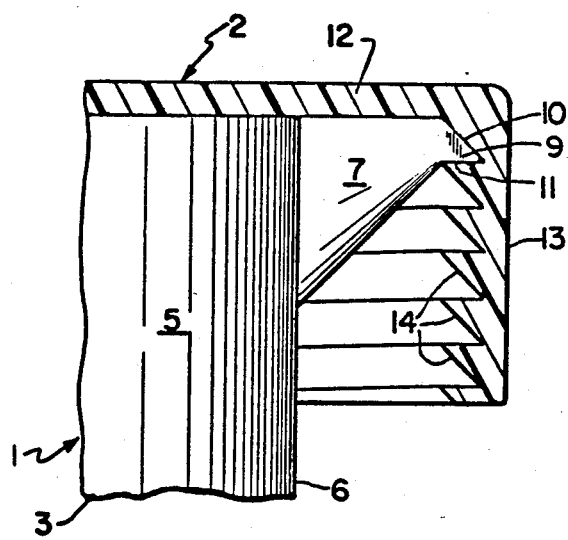
FIG. 5A is a fragmentary view, enlarged with respect to FIG. 5, showing a portion of the cover and upper end portion of the body after the cover has been rotated to fully applied and sealed position.

It is most advantageous to practice the method in connection with containers according to FIGS. 1–5A, the container comprising a hollow container body, indicated generally at 1, and removable cover, indicated generally at 2. Body 1 comprises a side wall 3 and a bottom wall 4 and is an integral piece, advantageously formed by injection molding from a relatively rigid thermoplastic polymeric material such as polystyrene. Side wall 3 includes a first portion 5 which is generally right circular cylindrical, save for the draft angle necessary for removal from the mold. The side wall also includes a flat portion 6 which lies in a plane which is chordal with respect to circles centered on the longitudinal axis of body 1, chordal portion 6 extending for the full length of body 1. At the upper end portion of the side wall, portion 6 has an integrally formed pouring spout 7 which opens upwardly, communicates with the interior of the container body, and is generally triangular in top plan elevation and in vertical cross section. The upper end portion of side wall 3 is provided with integrally formed external retaining rib means, in this embodiment having the form of buttress threads 8. Threads 8 are continuous throughout the circular extent of side wall portion 5 but are interrupted by chordal portion 6. Tip 9 of pouring spout 7 has in side elevation a configuration and size matching the cross-sectional shape and size of one turn of threads 8, and the tip is so located as to act as a portion of the threads. Thus, as best seen in FIG. 5A, tip 9 has an upper face 10 inclined downwardly and outwardly at the same angle as are the upwardly directed flanks of threads 8. Tip 9 also has a lower face 11 which is generally horizontal when the container is upright, and the dimensions of the tip are such that the tip, in effect, constitutes a segment of one turn of the buttress threads 8.

Cover 2 is also formed as an integral piece, as by injection molding, from a thermoplastic polymeric material (typically polypropylene) having significant resilient flexibility. The cover includes a flat circular main wall 12 and a dependent right circular cylindrical skirt 13, the skirt having internal threads 14 of size and configuration to mate with threads 8. The diameter of threads 14 is such that threads 14 will mate with the combination of threads 8 and spout tip 9. The resilient flexibility of the cover is such that, when the cover is centered on body 1 and pushed downwardly against the body, skirt 13 is outwardly deformed resiliently and the female buttress threads of the cover pass over the male threads of the container body until, as seen in FIG. 5, the lower face of main wall 12 of the cover is immediately adjacent the upper edge of side wall 3 of the container body. The threads are fully mated by a small rotation of the cover relative to the container body, the action of the threads forcing the lower face of main wall 12 into flush contact with the upper edge of side wall 3, as seen in FIG. 5A. Considering FIGS. 2 and 3, it will be noted that the upper edge of the side wall of the container body, including the upper edge of the pouring spout, lies in a plane transverse to the longitudinal axis of the container body, so that final mating of threads 8 and 14 results in flush contact of the main wall of the cover with the entire upper edge of the container body. Thus, simply pushing the cover into place, followed by tightening through a partial turn of the cover relative to the container body, closes both the container proper and the pouring spout against escape of liquid. As an added advantage, inclined surface 10 of the tip of the pouring spout, intersecting face 11 in a sharp corner, renders the pouring spout substantially drip free.

Figure 1:
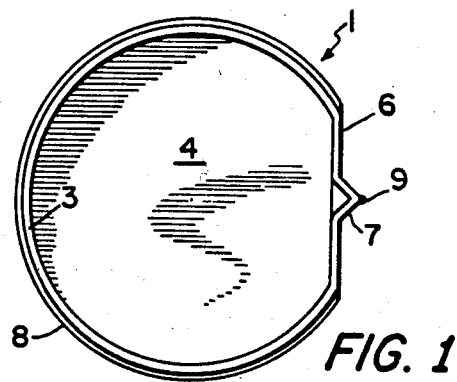
FIG. 1 is a top plan elevational view of one form of container body in connection with which the method can be practiced.
Figure 4:
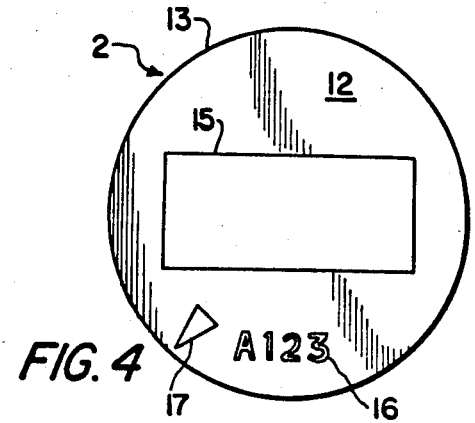
FIG. 4 is a top plan elevational view of the cover for the container body of FIGS. 1-3.
Figure 2:
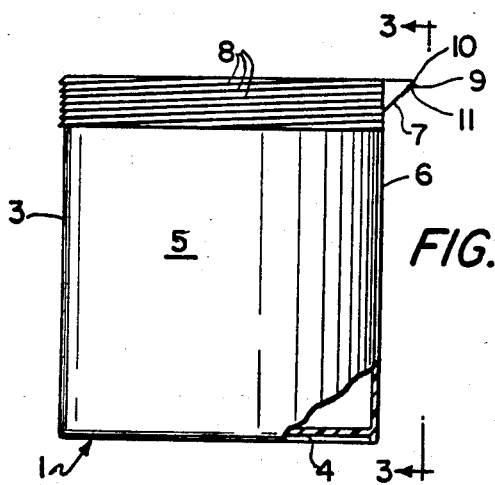
FIG. 2 is a side elevational view of the container body with a portion broken away for clarity of illustration.
Figure 3:
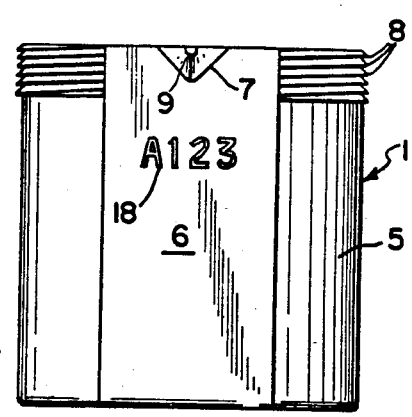
FIG. 3 is a side elevational view taken generally on line 3—3, FIG. 2.

The upper face of main wall 12 of the cover is provided with both a patient identification, as by making an elongated rectangular area 15 of that surface frosted so as to accept handwriting with a felt tip pen or other writing instrument, and with a permanent serial number 16, the serial number being parallel to the length of rectangular area 15 and applied in any conventional fashion, as by hot stamping or use of a permanent adhesive label. Simultaneously with application of serial number 16, a reference mark 17 is also applied to the upper face of wall 12 near the periphery of the cover, mark 17 being angularly displaced from serial number 16 by a distance and in a direction such that, when cover 2 is pushed into place while mark 17 is centered above pouring spout 7 and then turned to complete tightening of the screw threads, serial number 16 will be approximately centered with respect to side wall portion 6. A second serial number 18 is permanently applied to side wall portion 6 in a location centered on and spaced a substantial distance below pouring spout 7, as seen in FIG. 3. Then, whenever the cover has been properly applied to the container body, even a quick glance is adequate to determine that the cover, bearing the patient's name in addition to the serial number, matches the container body, and confusion between specimens from two different patients as a result of inadvertent interchange of the covers is avoided.

PRACTICING THE METHOD WITH CONTAINERS ACCORDING TO FIGS. 1–5A

Figure 6:
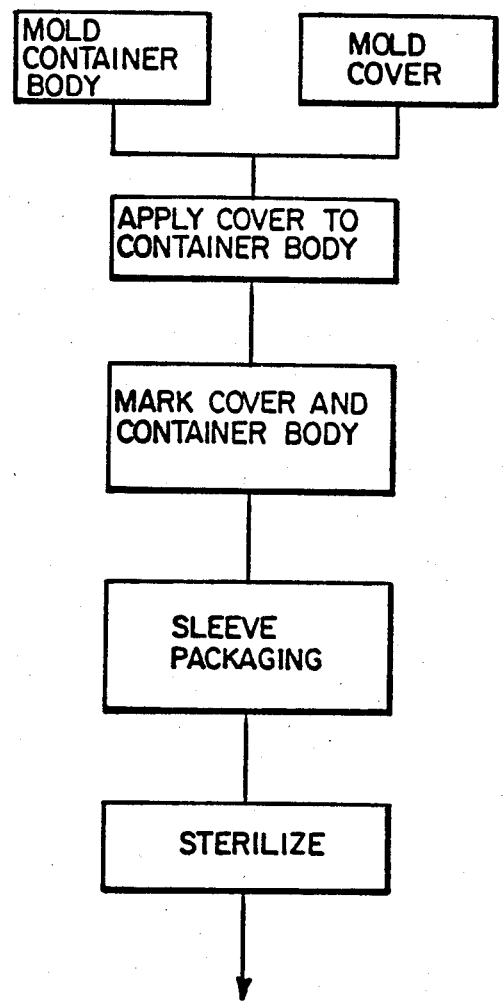
FIG. 6 is a flow sheet illustrating the method by which the container bodies and covers are serialized according to the invention.

The flow sheet of FIG. 6 illustrates one particularly advantageous method for producing containers according to the invention and will be described with reference to production of the container shown in FIGS. 1–5A. Container body 1 and cover 2 are formed in separate molds by injection molding from polystyrene crystal, with the mold for cover 2 constructed to provide frosted area 15 conventionally. The containers and covers are separately delivered to station A where each cover is applied to a container body, with application being such that, with the cover applied and threads tightened, the long dimension of frosted area 15 is parallel to chordal wall portion 6 of the container body. Thus assembled, each container is delivered to station B where serial number 16 and reference mark 17 are applied to the upper surface of wall 12 of the cover, with serial number 16 centered over spout 7 and and mark 17 displaced angularly from the serial number by that distance equal to the rotation of the cover necessary to tighten the threads 8, 14 when the cover has been forced down upon the container body, to bring the threads into engagement, when mark 17 is centered on spout 7. Serial number 16 and mark 17 are applied to cover 2 simultaneously and, simultaneously with such application, serial number 18 is applied to the outer surface of wall portion 6 in a location centered on and spaced below spout 7, spacing of the serial number below the spout being sufficient to allow serial numbers 16 and 18 to be viewed simultaneously. The container, with cover remaining in place, is then packaged in a sleeve of polymeric film conventionally, at station C, then delivered to station D and subjected to conventional in-package sterilization.

What is claimed is:

1. The method for making a reclosable container for a patient's specimen with improved assurance that, once a specimen has been introduced into the container and the container then closed, the identity of the patient will not be lost, comprising molding from polymeric material as separate pieces both a hollow container body and a removable cover for closing the body, the container body having a side wall and a pouring spout which projects outwardly from the upper end portion of the side wall, the side wall including an outer surface portion constituting a display area located below the pouring spout, the cover being constructed and arranged to close the entire upper end portion of the container body including the pouring spout, the upper surface of the cover constituting a display area;

delivering the container body and cover to an assembly station and, at the assembly station, applying the cover to the container body with the cover occupying a predetermined position relative to the body, in which position the cover closes the container body against spillage;

applying to the upper surface of the cover first permanent characteristic identifying indicia;

applying to the display area of the side wall of the container body second permanent identifying indicia, the first and second indicia being applied in predetermined locations while the cover remains in said predetermined position relative to the container body; and delivering the container body, with the cover still in place thereon, to a packaging station and packaging the container without removal of the cover.

2. The method according to claim 1, wherein the container body and cover are each molded with screw threads capable of coacting to retain the cover on the container body when the cover is applied to the container body;

the method further comprising applying a reference mark to the cover in a location which is spaced from the first indicia in advance of the first indicia by that distance necessary to tighten the screw threads when the cover is initially applied to the container body with the reference mark centered over the pouring spout, the step of applying the cover to the container body including the step of fully tightening the screw threads.

3. The method according to claim 1, wherein the upper end portion of the container body has a generally circular transverse cross section;

said outer surface portion of the side wall of the container body which constitutes a display area extends generally chordally with respect to the upper end portion of the container body; and the step of applying the second indicia to the display area of the side wall of the container body is carried out so that the second indicia is centered below the pouring spout.

4. The method according to claim 1, wherein the step of molding the cover is carried out to provide on the upper surface of the cover a defined area which is markable by a writing instrument, whereby the user of the container can write in said defined area the name of the patient providing the specimen, said defined area being elongated and extending generally parallel to the first indicia.

* * * * *